(12) United States Patent
Tamano et al.

(10) Patent No.: US 7,520,855 B2
(45) Date of Patent: Apr. 21, 2009

(54) BIOLOGICAL TISSUE ELASTICITY MEASUREMENT METHOD AND ULTRASONOGRAPHIC DEVICE

(75) Inventors: Satoshi Tamano, Chiba (JP); Takashi Osaka, Chiba (JP); Mitsuhiro Oshiki, Chiba (JP); Takeshi Matsumura, Chiba (JP); Tsuyoshi Shiina, Ibaraki (JP)

(73) Assignee: Hitachi Medical Corporation

( * ) Notice: Subject to any disclaimer, the term of this patent is extended or adjusted under 35 U.S.C. 154(b) by 589 days.

(21) Appl. No.: 10/532,707

(22) PCT Filed: Oct. 28, 2003

(86) PCT No.: PCT/JP03/13771
§ 371 (c)(1),
(2), (4) Date: Apr. 27, 2005

(87) PCT Pub. No.: WO2004/041092
PCT Pub. Date: May 21, 2004

(65) Prior Publication Data
US 2006/0058649 A1   Mar. 16, 2006

(30) Foreign Application Priority Data
Oct. 28, 2002 (JP) .............................. 2002-312023

(51) Int. Cl.
*A61B 8/00* (2006.01)
(52) U.S. Cl. .................. 600/437; 600/443; 600/447; 600/459; 382/128
(58) Field of Classification Search ......... 600/407–480; 382/128
See application file for complete search history.

(56) References Cited

U.S. PATENT DOCUMENTS
5,462,058 A   10/1995   Yamada (Continued)

FOREIGN PATENT DOCUMENTS
JP   01-139093 A   5/1989

(Continued)

*Primary Examiner*—Ruth S Smith
*Assistant Examiner*—Nasir Shahrestani
(74) *Attorney, Agent, or Firm*—Antonelli, Terry, Stout & Kraus, LLP.

(57) ABSTRACT

An ultrasonographic apparatus includes: an ultrasonic probe 1 for transmitting/receiving an ultrasonic wave to/from a patient, means 2 for generating an ultrasonic transmission signal and transmitting it to the ultrasonic probe, means 3 for receiving a reflection echo signal received by the ultrasonic probe; means 4 for re-constructing a form image according to the reception signal processed by the reception processing means; means 5 for re-constructing an elasticity image according to the reception signal processed by the reception processing means; means 7 for displaying the form image and the elasticity image; means 8 for switching between the form image mode and elasticity image mode; and means 9 for performing control so as to selectively acquire the form image and the elasticity image in the measurement period of the elasticity image mode switched by the mode switching means. Thus, it is possible to perform measurement associated with acquisition of both the form image and the elasticity image of the biological tissue and improve the image quality of the form image such as a B mode image and the image quality of the elasticity image such as elasticity ratio and elasticity distortion.

19 Claims, 8 Drawing Sheets

U.S. PATENT DOCUMENTS

| | | | |
|---|---|---|---|
| 5,538,004 A * | 7/1996 | Bamber | 600/443 |
| 5,606,971 A * | 3/1997 | Sarvazyan | 600/438 |
| 6,558,324 B1 * | 5/2003 | Von Behren et al. | 600/440 |

FOREIGN PATENT DOCUMENTS

| | | |
|---|---|---|
| JP | 02-142550 A | 5/1990 |
| JP | 7-303644 | 11/1995 |
| JP | 10-258054 A | 9/1998 |
| JP | 2003-111759 | 4/2003 |

* cited by examiner

BIOLOGICAL TISSUE ELASTICITY MEASUREMENT METHOD AND ULTRASONOGRAPHIC DEVICE

TECHNICAL FIELD

The present invention relates to a biological tissue elasticity measurement method and ultrasonographic apparatus, and, in particular, to a measurement method and ultrasonographic apparatus for acquiring a high quality elasticity image such as an elasticity ratio and an elasticity distortion of the biological tissue of a patient and a high quality form image of the biological tissue.

BACKGROUND ART

An ultrasonographic apparatus irradiates an ultrasonic wave to the patient by using an ultrasonic probe, measures the acoustic characteristic of a biological tissue within the patient by using the reflection echo signal, re-constructs a form image (such as a B-mode image and an M-mode image) of the biological tissue, for example, based on a difference or change in acoustic characteristic of an arbitrary area of the patient and displays the form image on a screen for a diagnosis.

Recently, it has been proposed that the ultrasonographic apparatus is used to measure elasticity information including either elasticity ratio or elasticity distortion, for example, of a biological tissue of a part to be diagnosed and display it as an elasticity ratio image or elasticity distortion image (each of which will be generally called elasticity image, hereinafter) (in Japanese Unexamined Patent Application Publication No. JP/P2000-60853A, for example). According to this, the form image of the biological tissue of the patient and the elasticity image such as the elasticity ratio and elasticity distortion, for example, are acquired simultaneously or alternately, and the form image and the elasticity image are displayed in line or one over another on one screen.

However, the ultrasonographic apparatus disclosed in the publication does not consider a measurement method for acquiring both high quality form and elasticity images.

DISCLOSURE OF INVENTION

An ultrasonographic apparatus of the present invention includes an ultrasonic probe for transmitting/receiving an ultrasonic wave to/from a patient, a unit for generating an ultrasonic transmission signal and transmitting it to the ultrasonic probe, a unit for performing reception processing on a reflection echo signal received by the ultrasonic probe, a unit for re-constructing a form image according to the reception signal processed by the reception processing unit, a unit for re-constructing an elasticity image according to the reception signal processed by the reception processing unit, a unit for displaying the form image and the elasticity image, a unit for switching between the form image mode and the elasticity image mode, and a unit for performing control so as to selectively acquire the form image and the elasticity image in the measurement period of the elasticity image mode switched by the mode switching unit.

Thus, both of high quality form and elasticity images can be acquired since, according to the present invention, the unit is provided for performing control so as to selectively acquire the form image and the elasticity image in the measurement period of the elasticity image mode switched by the mode switching unit, that is, in the measurement period of the elasticity diagnosis mode.

In this case, an ultrasonic transmission signal is applied which has an amplitude, wave number or frequency preferable for each of the form image measurement and the elasticity image measurement as the ultrasonic transmission signal for each of the measurement. More specifically, there may be provided a first transmission signal generating unit for generating an ultrasonic transmission signal for the form image, and a second transmission signal generating unit for generating an ultrasonic transmission signal for the elasticity image having at least one ultrasonic wave among an ultrasonic wave having a larger amplitude, an ultrasonic wave having a larger wave number and an ultrasonic wave having a lower frequency than those of the ultrasonic transmission signal for the form image. As a result, the image quality of the form image such as a B-mode image and the quality of the elasticity image such as an elasticity ratio and an elasticity distortion can be improved, and images suitable for both of the diagnoses can be provided.

The control unit may switch between the form image re-construction unit and the elasticity image re-construction unit according to the selection of the form image or the elasticity image. Also, the control unit may switch between the first transmission signal generating unit and the second transmission signal generating unit.

The reception processing unit may have a first reception processing unit for the form image for performing processing with a dynamic filter having a filter characteristic dependent on the depth of the reflection echo signal, and a second reception processing unit for the elasticity image for performing processing with a filter having a constant filter characteristic independent of the depth of the reflection echo signal. In this case, the control unit may switch between the first reception processing unit and the second reception processing unit according to the selection of the form image or the elasticity image.

The control unit can perform the switching for each frame of each image or for each ultrasonic beam to be irradiated to a patient according to the selection of the form image or the elasticity image. For example, when a focus area of elasticity image measurement is defined, the control unit may switch the control for each ultrasonic beam to be irradiated to the patient and cause the ultrasonic beam to scan. In this case, the elasticity image re-construction unit may re-construct the elasticity image of the focus area and display it over the form image on a display unit. The display unit can be configured to selectively display one image of a form image and an elasticity image, an image having both of them one over another, and an image having both of them in line.

A method for measuring an elasticity of a biological tissue of the present invention includes the steps of generating an ultrasonic transmission signal and transmitting it to an ultrasonic probe, performing reception processing on a reflection echo signal received by the ultrasonic probe, re-constructing at least one of a form image and an elasticity image according to the reception signal having undergone the reception processing, displaying at least one of the form image and the elasticity image, switching between a form image mode and an elasticity image mode, and controlling so as to selectively acquire the form image and the elasticity image in the measurement period of the elasticity image mode switched by the step.

BEST MODE FOR CARRYING OUT THE INVENTION

Figure 1:
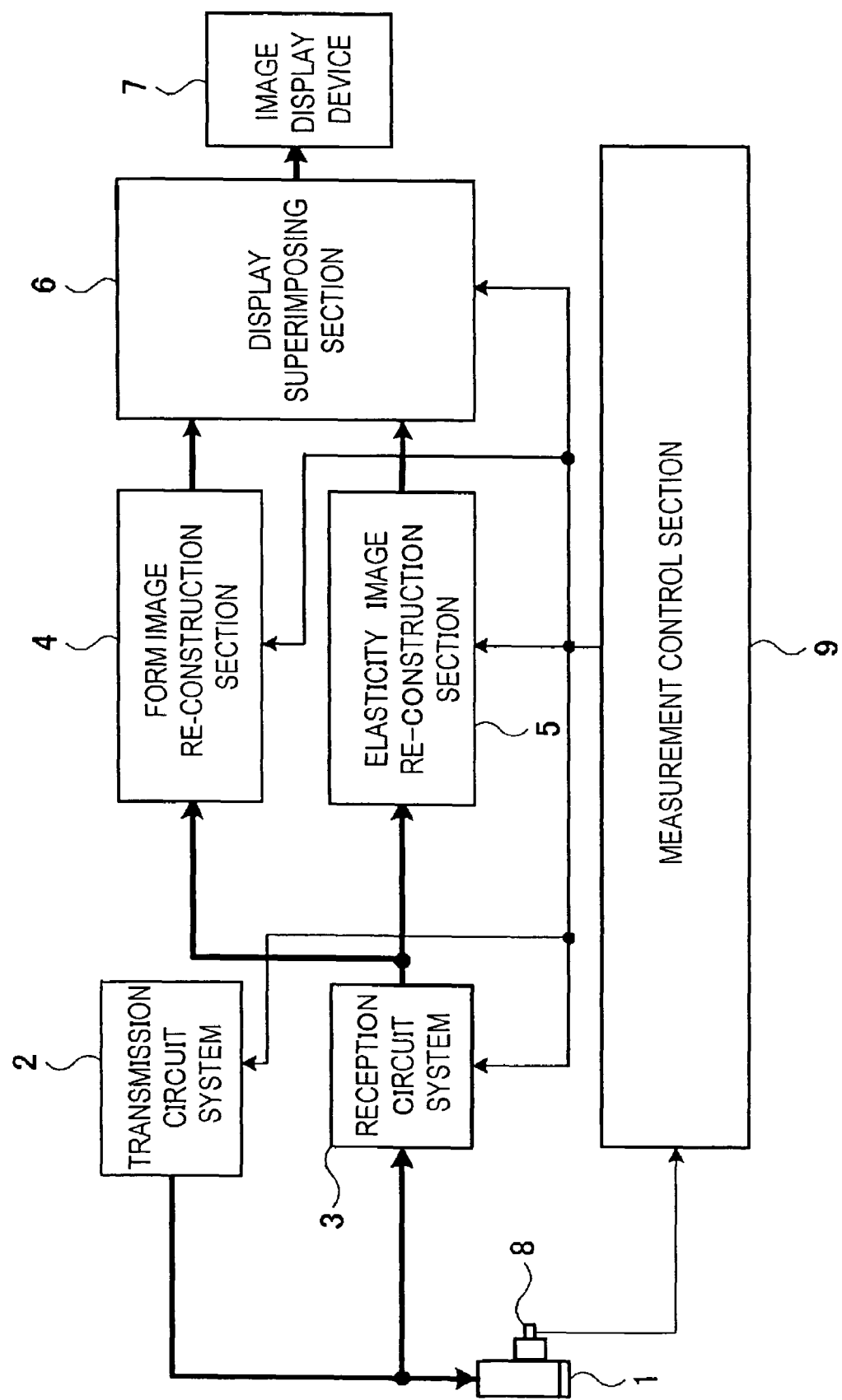
FIG. 1 is a block construction diagram of an embodiment of an ultrasonographic apparatus of the present invention.
Figure 2:
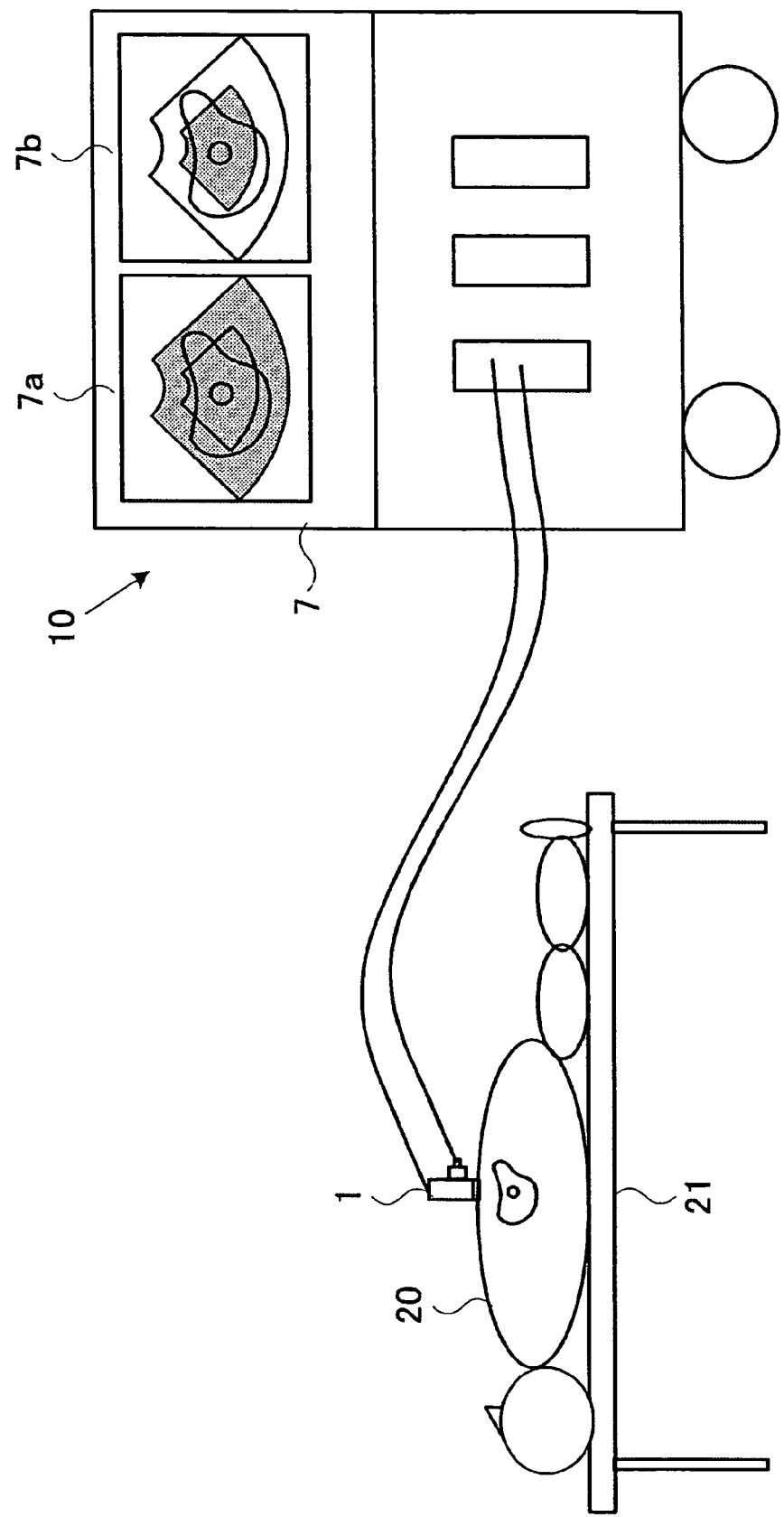
FIG. 2 is a diagram showing a relationship between the ultrasonographic apparatus of the present invention and a patient.

Embodiments of the present invention will be described below with reference to attached drawings. FIG. 1 is a block construction diagram of one embodiment of an ultrasonographic apparatus of the present invention. In FIG. 1, the thick line indicates a flow of an ultrasonic transmission/reception signal, and the thin line indicates a flow of a control signal. FIG. 2 is a diagram showing a relationship between the ultrasonographic apparatus according to this embodiment and a patient. As shown in FIG. 2, a patient 20 is laid on a bed 21, and measurement is performed thereon by using an ultrasonic probe 1 in contact with the body surface of the patient 20. In order to measure an elasticity image, an organ, for example, of the patient 20 can be pressed by the ultrasonic probe 1. The ultrasonic probe 1 and the ultrasonographic apparatus 10 are connected via a probe cable. A form image 7a and an elasticity image 7b, for example, are displayed simultaneously on an image display device 7 of the ultrasonographic apparatus 10.

The ultrasonographic apparatus 10 includes a transmission circuit system 2 and reception circuit system 3 connected to the ultrasonic probe 1 and a form image re-construction section 4 and elasticity image re-construction section 5, to which a reception signal output from the reception circuit system 3 is transmitted. Data of form and elasticity images re-constructed by the form image re-construction section 4 and elasticity image re-construction section 5 are input to a display superimposing section 6. Image data formed by the display superimposing section 6 is input to the image display device 7 and is displayed on the display screen. A measurement control section 9 is configured to control the transmission circuit system 2, reception circuit system 3, form image re-construction section 4, elasticity image re-construction section 5 and display superimposing section 6 based on a command input from a switch 8 provided in the ultrasonic probe 1.

The ultrasonic probe 1 transmits/receives an ultrasonic wave to/from a measurement target part of the patient 20. In other words, the ultrasonic probe 1 has multiple transducers, which are aligned one-dimensionally or two-dimensionally, and has functions of transmitting an ultrasonic wave to the inside of the patient 20 and receiving an ultrasonic reflection echo wave from the inside of the patient 20.

The transmission circuit system 2 is a transmission unit for transmitting an ultrasonic signal having undergone transmission focus processing for giving a different delay time to each channel in driving the multiple transducers included in the ultrasonic probe 1 and transmitting ultrasonic waves to multiple channels. In the transmission circuit system 2, an optimum transmission focus processing for each of them according to a form image or an elasticity image can be switched in accordance with timing defined by the measurement control section 9, which will be described later. In particular, the transmission circuit system 2 has a transmission signal generating unit for generating an ultrasonic transmission signal for a form image and a transmission signal generating unit for generating an ultrasonic transmission signal for an elasticity image having at least one ultrasonic wave of ultrasonic waves having a larger amplitude, a higher wave number and a lower frequency than those of an ultrasonic transmission signal for a form image. The transmission signal generating units for form and elasticity images are switched for use based on a command from the measurement control section 9.

The reception circuit system 3 is a reception processing unit for performing processing for receiving a reflection echo signal output from the ultrasonic probe 1, and performs amplification processing and filtering processing and includes a phasing unit for performing reception focus processing. As well known, the reception focus processing captures reflection echo signals of multiple channels received by the multiple transducers of the ultrasonic probe 1 and gives a different delay time to each of the channels to perform the reception focus processing, that is, phasing processing. Especially, in the reception circuit system 3 according to this embodiment, switching to optimum reception focus processing for each of them according to a form image or an elasticity image can be performed in accordance with timing defined by the measurement control section 9, which will be described later. In particular, the reception circuit system 3 has a reception processing unit for a form image for performing processing by using a dynamic filter having a filter characteristic dependent on the depth of a reflection echo signal and a reception processing unit for an elasticity image for performing processing by using a filter having a constant filter characteristic independent of the depth of a reflection echo signal. The reception processing units for form and elasticity images are switched for use based on a command from the measurement control portion 9.

The form image re-construction section 4 performs various kinds of computing processing on a reception signal output from the reception circuit system 3 and creates and outputs a form image to the display superimposing section 6. In other words, the form image-reconstruction section 4 re-constructs a form image such as a B-mode image based on a reception signal output from the reception circuit system 3. According to this embodiment, a form image is re-constructed by using an output from the reception circuit system 3 within a form image acquirement period defined by the measurement control section 9, which will be described later.

The elasticity image re-construction section 5 performs various kinds of computing processing on a reception signal output from the reception circuit system 3 and creates and outputs an elasticity image to the display superimposing section 6. In other words, the elasticity image re-construction section 5 stores a reception signal output from the reception circuit system 4 in a frame memory, for example, performs correlation processing on two reception signals received after a time interval and obtains an amount of displacement of a biological tissue. An elasticity ratio or elasticity distortion of each part is obtained by performing differentiation on the obtained amount of displacement, and an elasticity image thereof is re-constructed. The obtained elasticity image is displayed on the image display device 7 through the display superimposing section 6. In this embodiment, an elasticity image is re-constructed by using an output from the reception circuit system 3 within an elasticity image acquirement period defined by the measurement control section 9, which will be described later.

The display superimposing section 6 processes image such that outputs from the form image re-construction section 4 and the elasticity image re-construction section 5 can be displayed one over another or selectively or separately and be output to the image display device 7 to display. In particular, in this embodiment, the methods for displaying on the image display device 7 are switched based on a command from the measurement control section 9. The image display device 7 includes a general CRT monitor, for example.

The measurement control section 9 is configured to control each of the implementation of elasticity image measurement for acquiring an elasticity image and the implementation of form image measurement for acquiring a form image. In other words, the measurement control section 9 switches between the elasticity image measurement and the form image measurement based on start and end commands for the elasticity diagnosis mode, which are input from the switch 8 associated with the ultrasonic probe 1. The switching is performed by controlling operations of the transmission circuit system 2, reception circuit system 3, form image re-construction section 4, elasticity image re-construction section 5 and display superimposing section 6. A human interface device such as a switch provided in the ultrasonographic apparatus 10 in FIG. 2, a foot switch, not shown, and a key board may be used instead of the switch 8, or together with the switch 8.

Here, the first embodiment relating to control of the elasticity diagnosis mode to be performed by the measurement control section 9 will be described with reference to FIGS. 3 to 5. When an operator presses and turns on the switch 8 associated with the ultrasonic probe 1 in order to start an elasticity diagnosis, this is input to the measurement control section 9 as an elasticity diagnosis mode start command. When the switch 8 is released and turned off, this is input to the measurement control section 9 as an elasticity diagnosis mode end command. Based on this, the measurement control section 9 controls the starting and ending of the elasticity diagnosis mode for performing a compound measurement of the elasticity image measurement and the form image measurement. On the other hand, in the elasticity diagnosis mode, the operator must perform an operation for pressing the ultrasonic probe 1 against the patient when the switch 8 associated with the ultrasonic probe 1 is turned on. Conversely, when the ultrasonic probe 1 is pressed against the patient in advance, the operator must perform an operation of lifting the ultrasonic probe 1 when the switch 8 is turned on. While the case that the operator directly performs the pressing of the ultrasonic probe 1 will be described here, the ultrasonic probe 1 may be mechanically pressed or lifted. In this case, the ultrasonic probe 1 may be pressed against the patient or the ultrasonic probe 1 pressed against the patient in advance may be lifted by using a machine for pressing down the ultrasonic probe 1 though the additionally prepared human interface device such as the switch 8. Furthermore, the starting and ending of the elasticity diagnosis mode may be controlled.

When the elasticity diagnosis mode start command is input, the measurement control section 9 controls the switching of the components to selectively measure the form image and the elasticity image until the end command is input, that is, in the period of the elasticity diagnosis mode. For example, as shown in FIG. 3, a sector measurement area (region of interesting) of the elasticity image 33 is defined in a sector measurement area of the form image 32 here. In the figure, B-start and B-end indicate a scanning start position of the form image measurement and scanning end position of the form image measurement, respectively. The scanning with an ultrasonic beam is performed in the direction indicated by the shown arrow 31. S-start and S-end indicates a scanning start position of the elasticity image measurement and scanning end position of the elasticity image measurement, respectively. In the figure, B corresponds to the form image measurement, and S corresponds to the elasticity image measurement.

Figure 3:
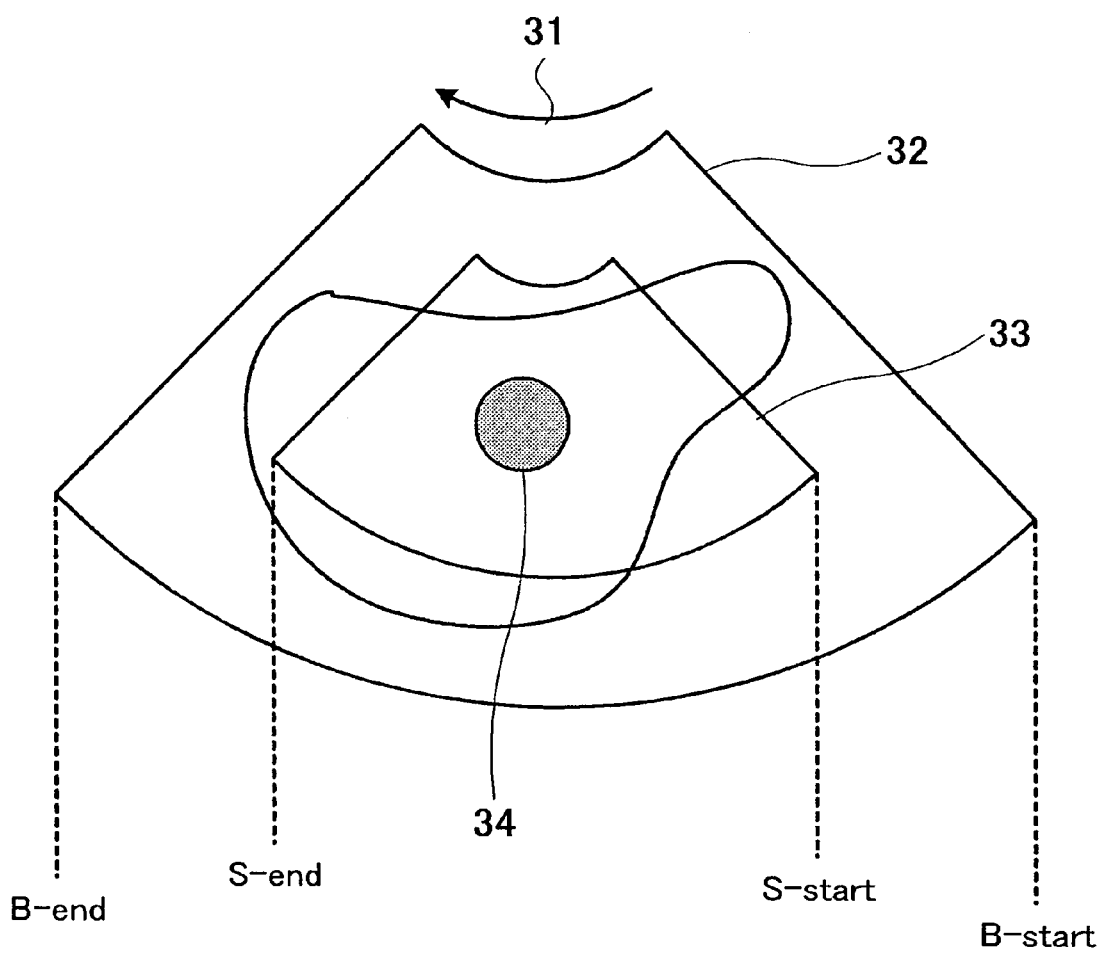
FIGS. 3 to 5 are diagrams showing an operation of a first embodiment of the present invention.
Figure 4:
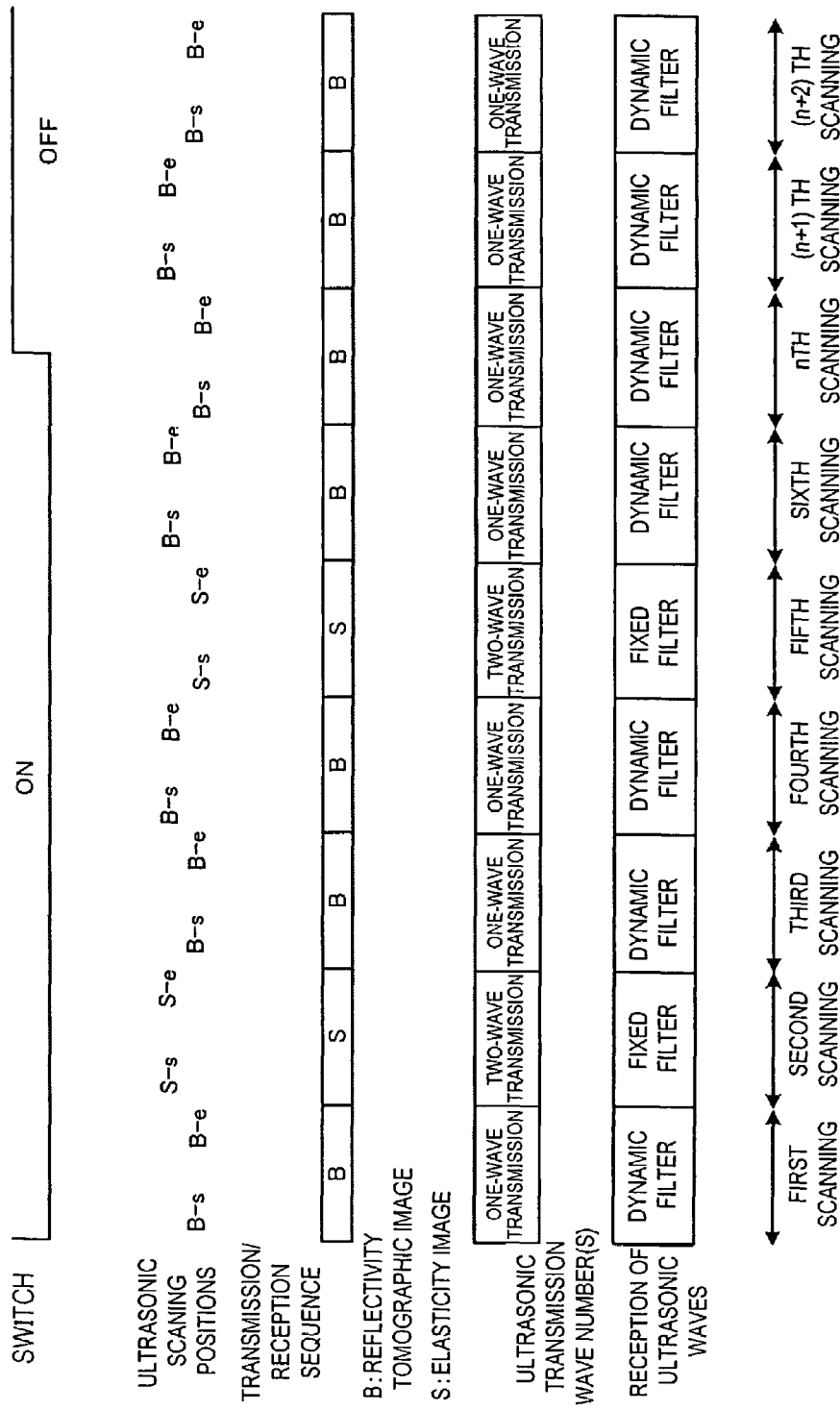

A timing chart for an operation of the measurement control section 9 for acquiring an image as shown in FIG. 3 is shown in FIG. 4. In the figure, changes in operational states of the "switch (8)", "ultrasonic scanning position", "transmission/reception sequence", "ultrasonic transmission wave number(s)" and "reception of ultrasonic waves" are shown in order from the top of the figure. The horizontal axis indicates the number of times of scanning; B corresponds to the form image measurement; S corresponds to the elasticity image measurement; and the subscripts s and e indicate the start and the end, respectively.

Figure 5:
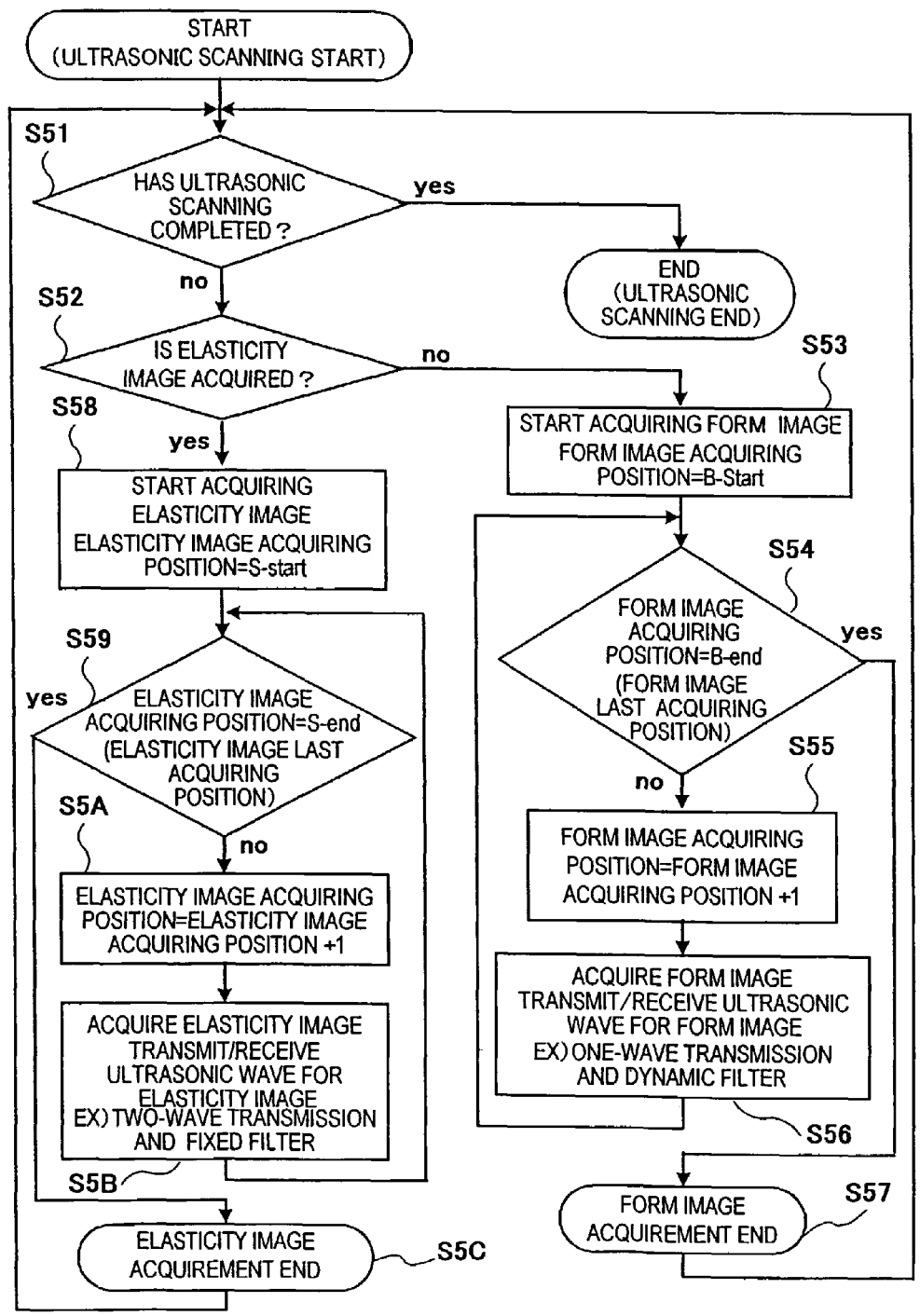

When the operator presses and turns on the switch 8 of the ultrasonic probe 1, the measurement control portion 9 starts measurement control of the elasticity diagnosis mode based on the timing chart in FIG. 4 and a flowchart shown in FIG. 5. In this embodiment, the transmission/reception sequence B of the form image measurement and the transmission/reception sequence S of the elasticity image measurement are switched and implemented by following predefined steps for each image frame, for example, in the period of the elasticity diagnosis mode when the switch 8 is kept on. In other words, each of the scanning from B-start to B-end and the scanning from S-start to S-end is handled as a unit for switching and implementation. In the shown example, after the form image measurement B is performed for one frame, the elasticity image measurement S is implemented for one frame. Then, after the form image measurement B is implemented for two frames, the elasticity image measurement S is implemented for one frame. However, the present invention is not limited to the ratio of the repetition in FIG. 4.

The measurement control section 9 switches and controls the transmission circuit system 2, the reception circuit system 3, the form image re-construction section 4, the elasticity image re-construction section 5 and the display superimposing section 6 based on the timing chart. First of all, when the elasticity diagnosis mode is started, the position of a predefined focus area for measuring the elasticity image 33 is captured. Then, the starting position (S-start) and ending position (S-end) of the elasticity image measurement are defined for the focus area. Next, the scanning for the form image measurement is started based on the timing chart in FIG. 4. At that time, a command for switching to an ultrasonic transmission signal (one-wave transmission in the example in FIG. 4) suitable for the form image measurement is output to the transmission circuit system 2. Moreover, a command for switching to reception processing with the dynamic filter is output to the reception circuit system 3, and a command for re-constructing the form image based on an input reception signal is output to the form image re-construction section 4. Thus, when the scanning of the form image measurement completes once, the processing is switched to the elasticity image measurement. The switching outputs a command for switching to an ultrasonic transmission signal (two-wave transmission in the example in FIG. 4) suitable for the elasticity image measurement to the transmission circuit system 2. Furthermore, a command for switching to reception processing with the fixed filter is output to the reception circuit system 3, and a command for re-constructing an elasticity image based on an input reception signal is output to the elasticity image re-construction section 5. However, the actual scanning for the elasticity image measurement is performed during the period from the S-start to S-end in FIG. 3. Thus, as shown in FIG. 4, the transmission/reception sequence is selected and implemented in order of B-S-B-B-S-B-B . . . . The elasticity image re-construction section 5 obtains an amount of displacement of a biological tissue by performing correlation processing on two reception signals having a time interval, which are obtained by the second and fifth scanning in FIG. 4, obtains an elasticity ratio or elasticity distortion based on the obtained amount of displacement and re-constructs the elasticity image. In this way, since the scanning of the form image measurement is performed twice during two measurement scans required for the elasticity image measurement, the amount of displacement of a biological tissue increases during the period. Therefore, the precision of measurement of an elasticity ratio or the like can be enhanced.

On the other hand, the measurement control portion 9 controls the display super imposing circuit 6 to cause the image display device 7 to selectively display the form image and the elasticity image newly created by the form image re-construction section 4 and the elasticity image re-construction section 5. A frame memory for storing a re-constructed image is provided in each of the form image re-construction section 4 and the elasticity image re-construction section 5. In order to perform the display control over the form image and the elasticity image, the measurement control section 9 does not input a reception signal for the elasticity image, which has undergone phasing processing in the reception circuit system 3, to the form image re-construction section 4 during the period for acquiring the elasticity image data but controls outputs to cause the image display device 7 to display the form image using the form image data, which is previously acquired and stored in the frame memory, during the period. The elasticity image re-construction section 5 is commanded not to capture a reception signal for a form image, which has undergone phasing processing in the reception circuit system 3 during the period for acquiring the form image data, and outputs are controlled to cause the image display device 7 to display the elasticity image using the elasticity image data, which is previously obtained and stored in the frame memory, during the period. Thus, in the form image measurement and elasticity image measurement, optimum transmission and reception processing for each of them is performed. Then, when the switch 8 is turned off, the measurement for the elasticity diagnosis mode ends. Notably, until the switch 8 is turned on again, control can be performed to repeat the form image measurement and display the latest form image on the image display device 7 and to display a previously acquired elasticity image on the image display device 7 as the elasticity image.

The control operation by the measurement control section 9 for implementing measurement control shown in the timing chart in FIG. 4 will be described by using the flowchart shown in FIG. 5. First of all, in step S51, whether the ultrasonic scanning is to be ended or not is determined. If not (No), the processing moves to step S52. If so (yes), ultrasonic scanning processing ends immediately.

In step S52, whether the current period is the period for elasticity image measurement, that is, for the elasticity image measurement S or not is determined. If yes, the processing moves to step S58. If no, the processing moves to step S53. B-start is stored in the form image acquirement position register in step S53 in order to start the acquirement of the form image since it is determined in previous step S52 that the current period is not the period for the elasticity image measurement S. In step S54, whether the value of the form image acquirement position register is B-end, that is, the final form image acquirement position or not is determined. If the determination results in yes, the processing moves to step S57 where the acquirement of the form image data ends. Then, the processing returns to step S51. If the determination results in no, the processing moves to step S55. In step S55, the value of the form image acquirement position resister is incremented by 1. In other words, the ultrasonic beam line address is shifted by one in the direction of scanning. In step S56, one-wave transmission, for example, is performed thereon with an ultrasonic transmission signal for the form image measurement. Furthermore, reception signal processing by using a dynamic filter is performed thereon, and the form image measurement is implemented. Then, the processing returns to step S54. In this way, by performing reception signal processing by using a dynamic filter, the reception frequency can be adjusted according to the depth of reception so that ultrasonic transmission/reception suitable for the form image acquirement can be performed. The processing in steps S54 to S56 can scan the form image 32 in the scanning direction 31 from the position B-start, and the form image 32 to the position B-end can be acquired.

In step S58, S-start is stored in the elasticity image acquiring position register to start elasticity image measurement since it is determined in previous step S52 that the current time is in the period of the elastic image acquiring time (S). In step S59, whether the value of the elasticity image acquiring position register is S-end or not, that is, whether it indicates the last acquiring position of the elasticity image or not is determined. If the determination results in yes, the processing moves to step S5C where the acquirement of the elasticity image data ends. Then, the processing returns to step S51. If no, the processing moves to step S5A. In step S5A, the value of the elasticity image acquiring position register is incremented by 1. That is, the ultrasonic beam line address is shifted by one in the scanning direction. In step S5B, two-wave transmission and reception signal processing using a fixed filter are performed, for example, with an ultrasonic transmission signal for elasticity image measurement so that the elasticity image acquiring processing by elasticity image measurement can be implemented. Then, the processing returns to step S59. By performing the two-wave transmission, ultrasonic transmission suitable for elasticity image measurement is performed. By performing ultrasonic reception by using a fixed filter, ultrasonic transmission/reception suitable for elasticity image acquirement can be performed with a constant reception frequency. The processing in steps S59 to S5B scans the elasticity image 33 in the scanning direction 31 from the position S-start, and the elasticity image 33 to the position S-end can be acquired. In the example in FIG. 3, an affected part 34 is displayed in the elasticity image 33. Upon completion of the acquirement of the elasticity image 33, the determination in step S51 is performed again, and the processing for acquiring the form image 32 or elasticity image 33 is performed according to the result. When an operator releases (switches off) the switch 8, the processing is shifted to a processing operation in an independent measurement mode for acquiring a form image until the switch 8 is pressed again.

The form image measurement and elasticity image measurement can be performed under each independent and proper ultrasonic transmission requirement since the transmission circuit system 2 includes, like the above-described embodiment, the transmission signal generating unit for generating an ultrasonic transmission signal for a form image and the transmission signal generating unit for generating an ultrasonic transmission signal for an elasticity image having a larger wave number than that of the ultrasonic transmission signal for a form image. As a result, ultrasonic images optimum for both form image and elasticity image can be re-constructed and displayed, and images suitable for a diagnosis can be provided to an operator. The image quality can be improved by selectively controlling the form image measurement and elasticity image measurement in the period of the elasticity diagnosis mode.

The quality of a form image can be further enhanced since the reception circuit system 3 includes and switches between a form image reception processing unit for processing with a dynamic filter having a filter characteristic (frequency characteristic) dependent on the depth of a reflection echo signal and an elasticity image reception processing unit for processing with a filter having a constant filter characteristic independent of the depth of a reflection echo signal.

While the case that the signal strength of a reception signal relating to an elasticity image is increased by using an ultrasonic transmission signal with a higher wave number in acquiring elasticity image data has been described in the above-described first embodiment, ultrasonic transmission with a large amplitude may be used instead. Alternatively, an ultrasonic transmission signal with a low frequency (10 MHz for form image measurement and 7.5 MHz for elasticity image measurement) may be used. Alternatively, a combination of an ultrasonic wave with a large wave number, an ultrasonic wave with a high amplitude and an ultrasonic wave having a low frequency may be used as required. That is, since the amount of displacement of a biological tissue is generally small, an ultrasonic wave with a larger amplitude or a larger wave number or an ultrasonic wave with a lower frequency than that of the ultrasonic wave for acquiring a form image is desirably used in order to increase the precision of the detection of a particularly hard part. Conversely, the measurement for acquiring a form image by an ultrasonic wave with a large amplitude results in an excessively large ultrasonic reception signal, or the measurement by an ultrasonic wave with a large wave number results in a decrease in distance resolution.

Figure 6:
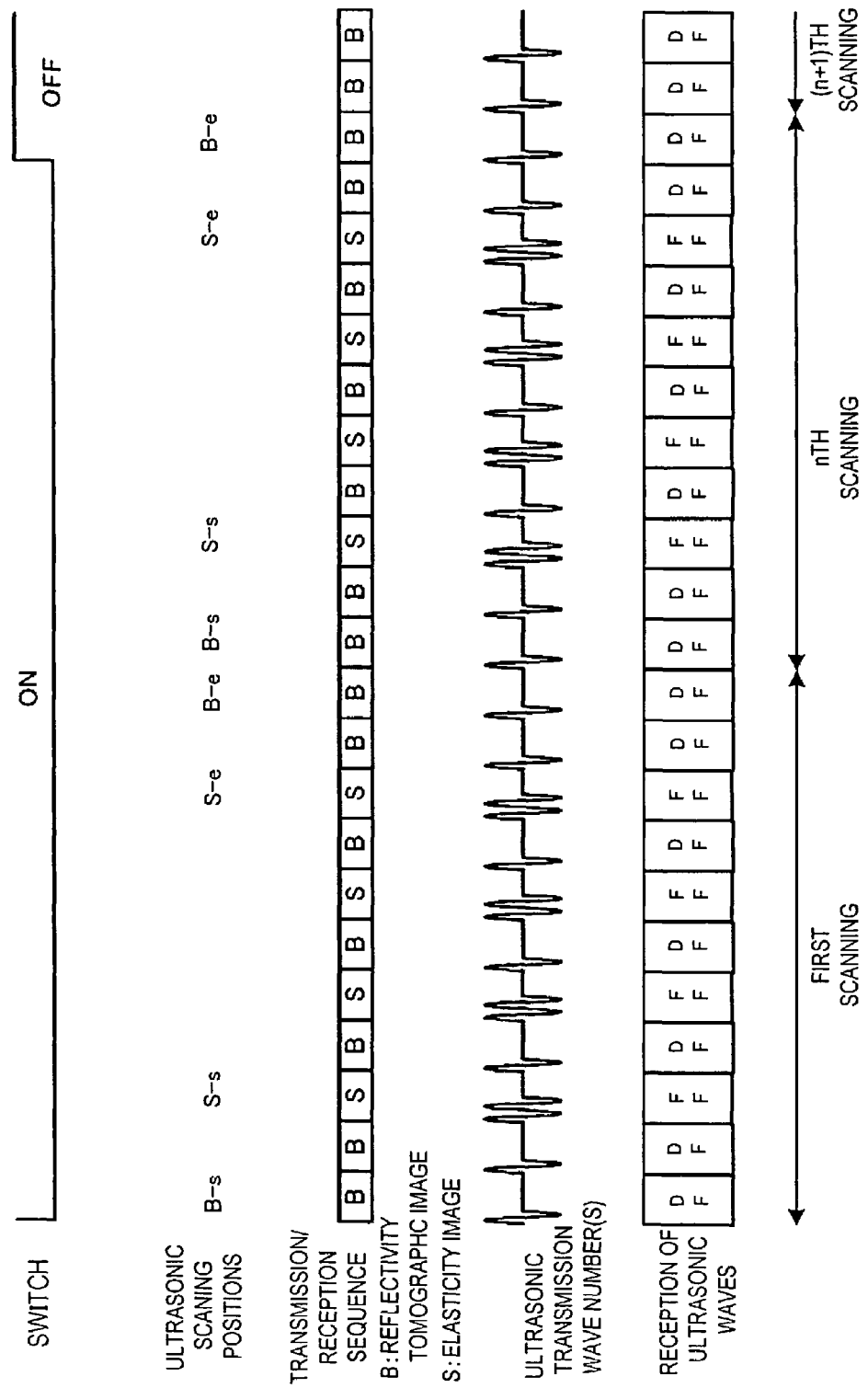
FIGS. 6 to 9 are diagrams for explaining an operation of a second embodiment of the present invention.
Figure 7:
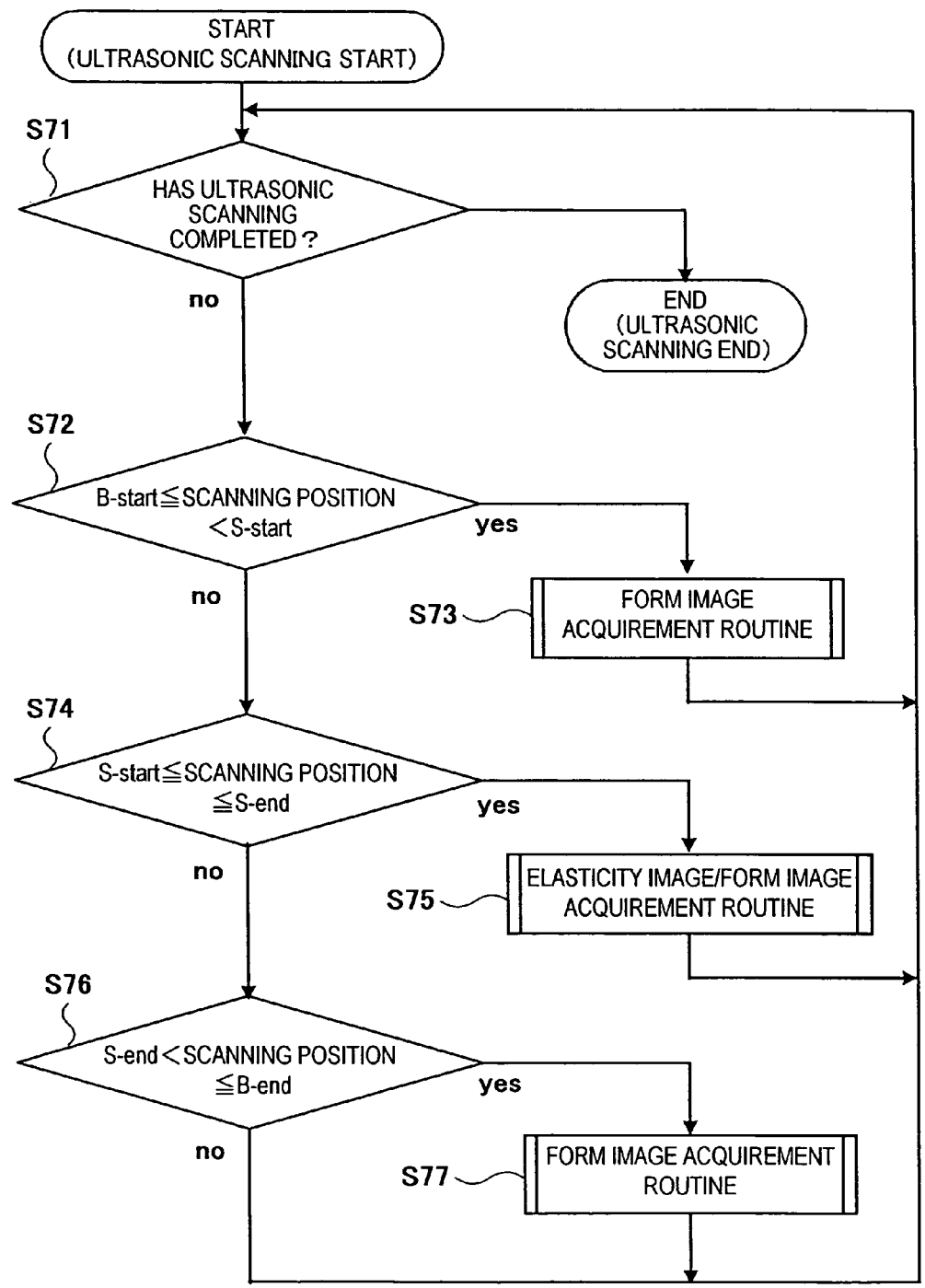
Figure 8:
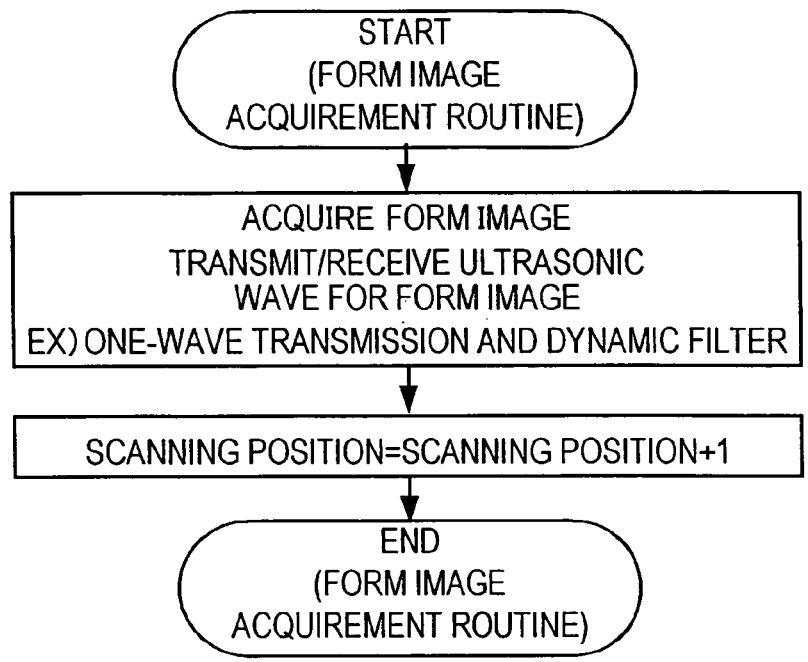
Figure 9:
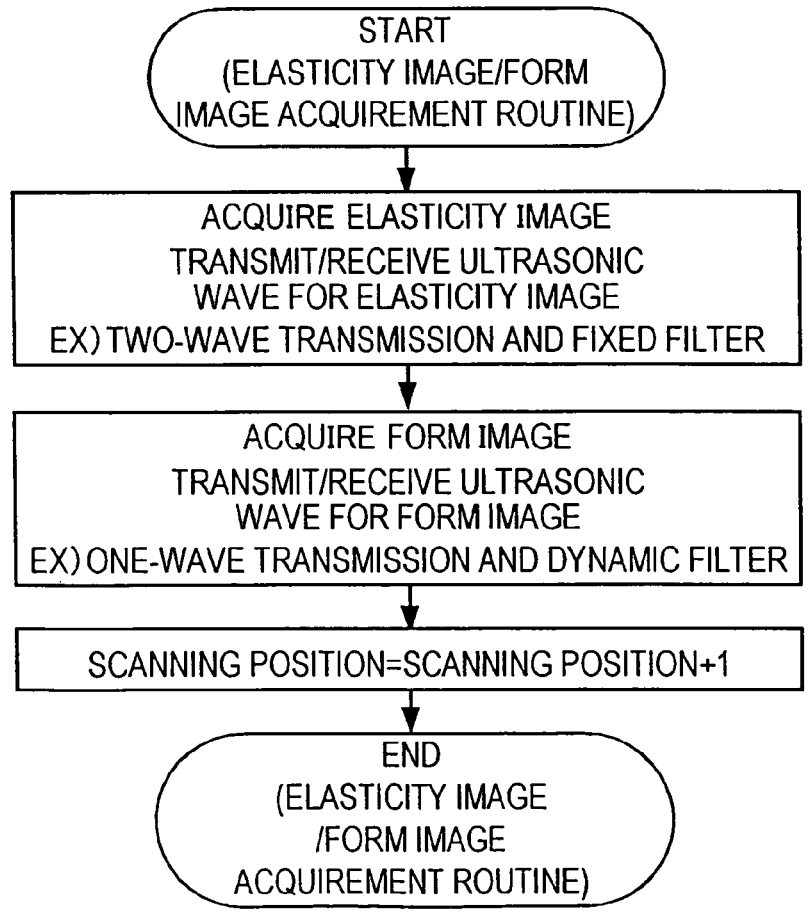

Next, a second embodiment relating to control of an elasticity diagnosis mode to be performed by the measurement control section 9 will be described with reference to FIGS. 6 to 9. FIG. 6 is a timing chart of an operation. FIGS. 7 to 9 are flowcharts illustrating details of the operation. FIG. 6 shows, like FIG. 4, changes in states of "switch (8)", "ultrasonic scanning position", "transmission/reception sequence", "ultrasonic transmission wave number(s)" and "reception of ultrasonic waves" in order from the top of the figure. The horizontal axis indicates the number of times of scanning, and DF and FF indicate a dynamic filter and a fixed filter, respectively. The meaning of the other symbols is identical to those of FIG. 4. This embodiment is different from FIG. 4 in that the form image measurement and elasticity image measurement are selectively switched not for each image frame but for each ultrasonic beam.

As shown in FIG. 6, during form image measurement B, an ultrasonic transmission signal with one wave number is output from the transmission circuit system 2, and reception processing is implemented by using a dynamic filter (DF) in the reception circuit system 3. On the other hand, during elasticity image measurement S, an ultrasonic transmission signal with two wave numbers is output from the transmission circuit system 2, and reception processing is implemented by using the fixed filter (FF) in the reception circuit system 3. Thus, for the form image measurement and elasticity image measurement, transmission and reception processing optimum for the image processing thereof can be implemented.

The measurement control section 9 repeatedly implements elasticity image measurement and form image measurement with different ultrasonic beam scanning positions in the elasticity image measurement S and form image measurement B. The elasticity image re-construction section 5 obtains an amount of displacement of a biological tissue by performing correlation processing on two reception signals having a time interval, which are obtained by the first and nth scanning in FIG. 6, obtains an elasticity ratio or elasticity distortion based on the obtained amount of displacement and re-constructs an elasticity image. When the measurement in the elasticity diagnosis mode ends based on a command from the switch 8, the measurement control section 9 controls to acquire form image data and to display a previously obtained and displayed elasticity image and the latest form image on the image display device 7.

Furthermore, the details will be described by following the flowcharts shown in FIGS. 7 to 9. When an operator presses and switches on the switch 8 of the ultrasonic probe 1, ultrasonic scanning start processing in FIG. 7 is started. Then, in step S71, whether ultrasonic scanning has ended or not is determined. If not (no), the processing moves to step S72. If so (yes), the ultrasonic scanning processing ends immediately.

In step S72, whether the value of the current scanning position register is the position equal to or higher than B-start and lower than S-start or not is determined. If yes, the processing moves to step S73. If no, the processing moves to next step S74. In step S73, a form image acquirement routine in FIG. 8 is implemented. The form image acquirement routine performs one-wave transmission, for example, with an ultrasonic transmission signal suitable for the form image measurement mode, performs reception signal processing by using a dynamic filter, implements form image acquirement processing in the form image measurement mode, increments the value of the scanning position register by 1 only and returns to step S71 in FIG. 7. The form image acquirement routine in step S73 is implemented to acquire form image data until the value of the scanning position register reaches S-start from B-start thereafter.

In step S74, whether the value of the current scanning position register is the position equal to or higher than S-start and is equal to or lower than S-end or not is determined. If yes, the processing moves to step S75. If no, the processing moves to next step S76. In step S75, an elasticity image/form image acquirement routine in FIG. 9 is implemented. The elasticity image/form image acquirement routine repeatedly implements an operation including acquiring elasticity data, implementing acquirement of form image data after the acquirement, performs elasticity image scanning again after a predetermined interval. That is, compound measurement is implemented on the area of the form image 33 corresponding to a focus area by switching between the form image measurement mode and the elasticity image measurement mode for each ultrasonic beam line address. In the elasticity image/form image acquirement routine, two-wave transmission is performed, for example, with an ultrasonic transmission signal suitable for the elasticity image measurement, and processing of a reception signal uses a fixed filter. One-wave transmission is performed, for example, with an ultrasonic transmission signal suitable for the form image measurement, and processing of a reception signal implements processing using a dynamic filter. Next, the value of the scanning position register is incremented by 1 only, and the processing returns to step S71 in FIG. 7. The elasticity image/form image acquirement routine in step S75 is implemented, and the scanning of a form image and the scanning of an elasticity image are alternately repeated to acquire the image until the value of the scanning position register reaches S-end from S-start thereafter.

In step S76, whether the value of the current scanning position register is a position higher than S-end and equal to or lower than B-end or not is determined. If yes, the processing moves to step S77. If no, the processing returns to step S71. That is, after the elasticity image scanning to the position S-end ends, the form image data acquirement is repeated up to the position B-end. In step S77, a form image acquirement routine in FIG. 8 is implemented. The form image acquirement routine performs one-wave transmission, for example, with an ultrasonic transmission signal suitable for form image measurement, implements reception processing using a dynamic filter, increments the value of the scanning position register by 1 only and returns to step S71 in FIG. 7. The form image acquirement routine in step S77 is implemented to acquire the form image 32 until the value of the scanning position register reaches S-start from S-end thereafter.

Then, the form image data acquirement is performed from B-start to B-end until an operator presses the switch 8 again. When the operator presses the switch 8 again, the processing returns to the beginning, and a series of operations from the form image scanning from the position B-start is repeated.

As described above, according to the second embodiment, the same advantages as those of the first embodiment can be obtained.

The invention claimed is:

1. An ultrasonographic apparatus, comprising:
an ultrasonic probe for transmitting/receiving an ultrasonic wave to/from a patient;
means for generating an ultrasonic transmission signal and transmitting it to the ultrasonic probe;
means for performing reception processing on a reflection echo signal received by the ultrasonic probe;
means for re-constructing a form image according to the reception signal processed by the reception processing means;
means for re-constructing an elasticity image according to the reception signal processed by the reception processing means;
means for displaying the form image and the elasticity image;
means for switching between the form image mode and the elasticity image mode; and
wherein the reception processing means includes first reception processing means for the form image and second reception processing means for the elasticity image; and
means for control between the first processing means and the second processing means;
wherein the control means switches between the first reception processing means and the second reception processing means according to selection of the form image and the elasticity image.

2. The ultrasonographic apparatus according to claim 1, wherein the control means switches between the form image re-construction means and the elasticity image re-construction means according to the selection of the form image or the elasticity image.

3. The ultrasonographic apparatus according to claim 1, wherein the transmission means has first transmission signal generating means for generating an ultrasonic transmission signal for the form image; and second transmission signal generating means for generating an ultrasonic transmission signal for the elasticity image having at least one ultrasonic wave among an ultrasonic wave having a larger amplitude, an ultrasonic wave having a larger wave number and an ultrasonic wave having a lower frequency than those of the ultrasonic transmission signal for the form image.

4. The ultrasonographic apparatus according to claim 3, wherein the control means switches between the first transmission signal generating means and the second transmission signal generating means according to the selection of the form image or the elasticity image.

5. The ultrasonographic apparatus according to claim 1, wherein:
the first reception processing means performs processing with a dynamic filter having a filter characteristic dependent on the depth of the reflection echo signal; and
the second reception processing means performs processing with a filter having a constant filter characteristic independent of the depth of the reflection echo signal.

6. The ultrasonographic apparatus according to claim 1, wherein the control means performs control, for each frame of each image, so as to selectively acquire the form image and the elasticity image.

7. The ultrasonographic apparatus according to claim 1, wherein the control means performs control, for each ultrasonic beam to be irradiated to the patient, so as to selectively acquire the form image and the elasticity image.

8. The ultrasonographic apparatus according to claim 1, wherein the control means switches, for each ultrasonic beam to be irradiated to the patient, control for selectively acquiring the form image and the elasticity image with respect to a defined focus area and causes the ultrasonic beam to scan; and the elasticity image re-construction means re-constructs the elasticity image of the focus area and displays it over the form image on the display means.

9. The ultrasonographic apparatus according to claim 1, wherein the control means switches, for each frame of each image or for each ultrasonic beam to be irradiated to the patient, control for selectively acquiring the form image and the elasticity image during the period from the time when a measurement start command of the elasticity image mode is input from the mode switching means to the time when a measurement end command is input therefrom.

10. The ultrasonographic apparatus according to claim 1, wherein the display means selectively displays one image of the form image and the elasticity image, an image having both of them one over another and an image having both of the in line.

11. The ultrasonographic apparatus according to claim 1, wherein the mode switching means is at least one of human interface equipment such as a switch provided in the ultrasonic probe, a switch provided in the apparatus body, a foot switch and a keyboard.

12. A method for measuring an elasticity of a biological tissue, comprising the steps of:
generating an ultrasonic transmission signal and transmitting it to an ultrasonic probe;
performing a step of reception processing on a reflection echo signal received by the ultrasonic probe by selectively controlling switching between a first reception mode and a second reception mode;
re-constructing a form image and an elasticity image based on the reception signal having undergone the reception processing;
displaying at least one of the form image and the elasticity image; and
switching between a form image mode and an elasticity image mode;
wherein the reception processing step switches between and performs first reception processing for the form image and second reception processing for the elasticity image according to the selection of the form image and the elasticity image.

13. The biological tissue elasticity measurement method according to claim 12, wherein the ultrasonic transmission signal for the elasticity image generated by the transmission step has at least one ultrasonic wave among an ultrasonic wave having a larger amplitude, an ultrasonic wave having a larger wave number and an ultrasonic wave having a lower frequency than those of the ultrasonic transmission signal for the form image.

14. The biological tissue elasticity measurement method according to claim 12 or 13, wherein the first reception processing is for performing processing with a dynamic filter having a filter characteristic dependent on the depth of the reflection echo signal and the second reception processing is for performing processing with a filter having a constant filter characteristic independent of the depth of the reflection echo signal.

15. The biological tissue elasticity measurement method according to claim 12, wherein the control step switches, for each frame of each image, between the ultrasonic transmission signals for the form image measurement and the elasticity image measurement.

16. The biological tissue elasticity measurement method according to claim 12, wherein the control step switches, for each ultrasonic beam to be irradiated to the patient, between the ultrasonic transmission signals for the form image measurement and the elasticity image measurement.

17. The biological tissue elasticity measurement method according to claim 12, wherein the control step scans an ultrasonic beam by the ultrasonic transmission signal for the elasticity image measurement with respect to a defined focus area; and the image re-construction step re-constructs the elasticity image of the focus area and displays it over the form image on the display means.

18. The biological tissue elasticity measurement method according to claim 12, wherein the control step switches, for each frame of each image or for each ultrasonic beam to be irradiated to the patient, control for selectively acquiring the form image and the elasticity image during the period from the time when a measurement start command of the elasticity image mode is input to the time when a measurement end command is input.

19. The biological tissue elasticity measurement method according to claim 12, wherein the measurement start and end commands of the elasticity image mode are input from at least one of human interface equipment such as a switch provided in the ultrasonic probe, a switch provided in the apparatus body, a foot switch and a keyboard.

* * * * *